US012605370B2

(12) United States Patent
Plas et al.

(10) Patent No.: US 12,605,370 B2
(45) Date of Patent: Apr. 21, 2026

(54) AGENTS AND COMPOSITIONS FOR THE TREATMENT OF GLIOBLASTOMA

(71) Applicant: University of Cincinnati, Cincinnati, OH (US)

(72) Inventors: David Plas, Cincinnati, OH (US); Kelli Ennis, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 740 days.

(21) Appl. No.: 17/910,202

(22) PCT Filed: Mar. 12, 2021

(86) PCT No.: PCT/US2021/022072
§ 371 (c)(1),
(2) Date: Sep. 8, 2022

(87) PCT Pub. No.: WO2021/183860
PCT Pub. Date: Sep. 16, 2021

(65) Prior Publication Data
US 2023/0124475 A1 Apr. 20, 2023

Related U.S. Application Data

(60) Provisional application No. 62/988,486, filed on Mar. 12, 2020.

(51) Int. Cl.

| | |
|---|---|
| ***A61K 31/4439*** | (2006.01) |
| ***A61K 9/00*** | (2006.01) |
| ***A61K 31/519*** | (2006.01) |
| ***A61K 45/06*** | (2006.01) |

(52) U.S. Cl.
CPC ........ *A61K 31/4439* (2013.01); *A61K 9/0019* (2013.01); *A61K 31/519* (2013.01); *A61K 45/06* (2013.01)

(58) Field of Classification Search
CPC .............. A61K 31/4439; A61K 9/0019; A61K 31/519; A61K 45/06
See application file for complete search history.

(56) References Cited

U.S. PATENT DOCUMENTS

2018/0371093 A1 12/2018 Bilic et al.

OTHER PUBLICATIONS

He et. al.; First-in-Human Phase I Study of Merestinib, an Oral Multikinase Inhibitor, in Patients with Advanced Cancer; The Oncologist, 2019, 24:e930-e942. (Year: 2019).*

Konicek et al.; Merestinib (LY2801653) inhibits neurotrophic receptor kinase (NTRK) and suppresses growth of NTRK fusion bearing tumors; Oncotarget, 2018, vol. 9, (No. 17), pp. 13796-13806. (Year: 2018).*

(Continued)

*Primary Examiner* — Kortney L. Klinkel
*Assistant Examiner* — Jackson J Hernandez
(74) *Attorney, Agent, or Firm* — Dinsmore & Shohl LLP

(57) ABSTRACT

Provided herein are compositions including a combination of therapeutic agents comprising a therapeutically effective amount of merestinib and a therapeutically effective amount of LY2584702. Also provided herein are methods of treating glioblastomas in a subject by administering the disclosed compositions, as well as methods of inducing cell death in a PTEN-deficient glioblastoma cell by administering the disclosed compositions.

19 Claims, 2 Drawing Sheets

(56) References Cited

OTHER PUBLICATIONS

International Search Report mailed on Jun. 4, 2021 in reference to co-pending Application No. PCT/US2021/22072 filed Mar. 12, 2021.

Written Opinion mailed on Jun. 4, 2021 in reference to co-pending Application No. PCT/US2021/22072 filed Mar. 12, 2021.

Bell et al. MNK Inhibition Disrupts Mesenchymal Glioma Stem Cells and Prolongs Survival in a Mouse Model of Glioblastoma, Molecular Cancer Research, Oct. 2016, vol. 14, No. 10, pp. 984-993.

Liu et al. Pharmacologic Targeting of S6K1 in PTEN-Deficient Neoplasia, Cell reports, Feb. 28, 2017, vol. 18, No. 9, pp. 2088-2095.

Tolcher et al. A phase I trial of LY2584702 tosylate, a p70 S6 kinase inhibitor, in patients with advanced solid tumours, European Journal of Cancer, Mar. 2014, vol. 50, No. 5, pp. 867-875.

Cetintas, V. B. et al. “Is there a casual link between PTEN deficient tumors and immunosuppresive tumor microenvironment?” Journal of Translational Medicine, Jan. 30, 2020, pp. 1-11, vol. 18, No. 1, https://doi.org/10.1186/s12967-020-02219-w.

EP Extended European Search Report dated Dec. 20, 2023 pertaining to EP application No. 21766896.1 filed Oct. 11, 2022, pp. 1-8.

* cited by examiner

AGENTS AND COMPOSITIONS FOR THE TREATMENT OF GLIOBLASTOMA

CROSS-REFERENCE TO RELATED APPLICATIONS

This application is a § 371 National Stage Application of International Application Serial No. PCT/US2021/022072, filed Mar. 12, 2021, and claims priority to U.S. Provisional Application Ser. No. 62/988,486, filed Mar. 12, 2020, each of which is incorporated herein by reference in its entirety.

TECHNICAL FIELD

The present disclosure relates to the field of cancer treatments, and more particularly, to compositions and methods for treating glioblastomas.

BACKGROUND

Glioblastoma, also known as glioblastoma multiforme (GBM), is an aggressive cancer that originates within the brain and can occur in the brain and/or spinal cord. Approximately 1 out of 5 brain tumors are glioblastomas. Glioblastomas generally have a very poor prognosis. Glioblastomas usually result in death within 12-15 months of diagnosis, and have a five-year survival rate of 3-7%.

Currently, there is no known method of preventing glioblastomas. Further, treatment of glioblastomas can be extremely difficult due to a variety of factors, including the brain's limited capacity for self-repair, difficulty in drugs passing the blood-brain barrier ("BBB"), potential of damage to the brain by use of conventional therapies (such as aggressive chemotherapy, radiation, and surgery), and difficulty in surgically removing all cancerous cells due to infiltration of the tumor throughout the brain. Due to the challenges in treating glioblastomas, most care for glioblastoma patients involves palliative care, care to help slow the spread, and other measures aimed at temporarily improving survival, as true cures from glioblastoma are rarely observed.

Thus, a need exists for further compositions and methods for the treatment of glioblastomas.

SUMMARY

Accordingly, provided herein are methods and compositions for the treatment of glioblastomas. Without being bound by theory, it is believed that the disclosed methods and compositions function in the glioblastoma subject by inducing cell death in phosphatase and tensin homolog (PTEN)-deficient glioblastoma cells.

In one embodiment, the present disclosure is directed to a method of inducing cell death in a phosphatase and tensin homolog (PTEN)-deficient glioblastoma cell, the method comprising administering to the cell a combination of therapeutic agents comprising: a therapeutically effective amount of merestinib and a therapeutically effective amount of LY2584702, wherein cell death of the glioblastoma cell is induced.

In another embodiment, the present disclosure is directed to a method of treating glioblastoma in a subject in need thereof, the method comprising administering to the subject a combination of therapeutic agents comprising: a therapeutically effective amount of merestinib and a therapeutically effective amount of LY2584702.

In another embodiment, the present disclosure is directed to a pharmaceutical composition comprising: a therapeutically effective amount of merestinib, a therapeutically effective amount of LY2584702, and one or more pharmaceutically acceptable excipients.

These and other objects, features, embodiments, and advantages will become apparent to those of ordinary skill in the art from a reading of the following detailed description and the appended claims.

BRIEF DESCRIPTION OF THE DRAWINGS

The details of embodiments of the presently disclosed subject matter are set forth in this document. Modifications to embodiments described in this document, and other embodiments, will be evident to those of ordinary skill in the art after a study of the information provided in this document.

DETAILED DESCRIPTION

Figure 1:
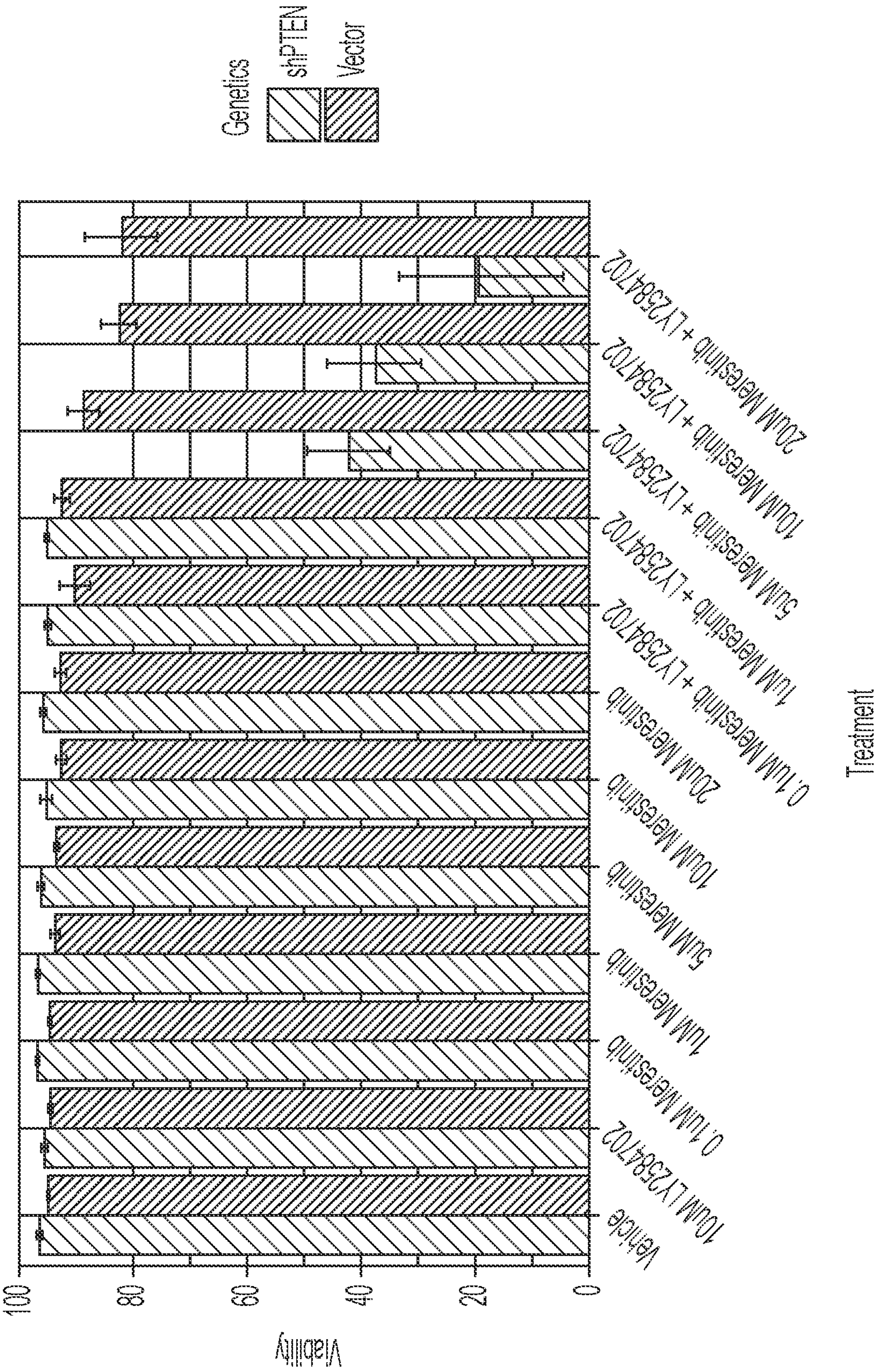
FIG. 1 depicts a dose curve analysis showing the efficacy of the combination of LY2584702 with merestinib in shPTEN LN229 glioblastoma cells. Viability was measured using CytoTox Glo after culturing with inhibitors in serum-free conditions for 72 hours.

The details of one or more embodiments of the presently disclosed subject matter are set forth in this document. Modifications to embodiments described in this document, and other embodiments, will be evident to those of ordinary skill in the art after a study of the information provided in this document.

The practice of the present invention will employ, unless otherwise indicated, conventional methods of virology, microbiology, molecular biology, and recombinant DNA techniques within the skill of the art. Such techniques are explained fully in the literature. See, e.g., Sambrook et al. *Molecular Cloning: A Laboratory Manual* (Current Edition); DNA Cloning: A Practical Approach, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology,* 2nd Edition, vol. I & II (B. N. Fields and D. M. Knipe, eds.); *Freshney Culture of Animal Cells, A Manual of Basic Technique* (Wiley-Liss, Third Edition); and Ausubel et al. (1991) *Current Protocols in Molecular Biology* (Wiley Interscience, N.Y.).

While the following terms are believed to be well understood in the art, definitions are set forth to facilitate explanation of the presently disclosed subject matter. Unless defined otherwise, all technical and scientific terms used herein have the same meaning as commonly understood by one of ordinary skill in the art to which the presently disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in this specification and the appended claims, the singular forms "a," "an" and "the" include plural references unless the content clearly dictates otherwise.

As used herein, the term "subject" refers to any mammalian subject, including humans, non-human primates, pigs, dogs, rats, mice, and the like. In a specific embodiment, the patient is a human patient.

The terms "treat," "treatment," and "treating," as used herein, refer to a method of alleviating or abrogating a disease, disorder, and/or symptoms thereof in a subject.

A "therapeutically effective amount" is an amount sufficient to achieve beneficial or desired results. A therapeutically effective amount can be administered in one or more administrations, applications or dosages. The therapeutically effective amount of the compounds and/or agents for use in the pharmaceutical compositions and methods herein will vary with the glioblastoma being treated, the age and physical condition of the subject to be treated, the severity of the condition, the duration of the treatment, the nature of concurrent therapy, the particular compounds and/or agents being employed, the particular pharmaceutically acceptable carriers utilized, and like factors within the knowledge and expertise of the attending physician. As will be appreciated by those of ordinary skill in this art, the therapeutically effective amount of a substance may vary depending on such factors as the desired biological endpoint, the substance to be delivered, the target cell or tissue, etc. For example, the therapeutically effective amount of a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Furthermore, a therapeutically effective amount may be administered via a single dose or via multiple doses within a treatment regimen. In some embodiments, individual doses or compositions are considered to contain a therapeutically effective amount when they contain an amount effective as a dose in the context of a treatment regimen. Those of ordinary skill in the art will appreciate that a dose or amount may be considered to be therapeutically effective if it is or has been demonstrated to show statistically significant effectiveness when administered to a population of patients; a particular result need not be achieved in a particular individual patient in order for an amount to be considered to be therapeutically effective as described herein.

Phosphatase and tensin homology (PTEN) is a protein phosphatase and multifunctional tumor suppressor that is encoded by the PTEN gene. PTEN mutation or deficiency is often associated with the development of many cancers, including glioblastomas. PTEN preferentially dephosphorylates phosphoinositide substrates, thereby negatively regulating intracellular phosphatidylinositol-3,4,5-trisphosphate levels and the AKT/PKB signaling pathway. As used herein "PTEN-deficient cells" are cells that do not express PTEN, or expresses PTEN at a significantly reduced level as compared to normal, healthy cells.

Ribosomal protein S6 kinase beta-1 (S6K1), also known as p70S6 kinase (p70S6K or p70-S6K), is a serine-threonine protein kinase encoded by the RPS6KB1 gene. S6K1 phosphorylates the S6 ribosomal protein, thereby inducing protein synthesis by the ribosome. Dysregulation of the S6K1 signaling, such as overexpression of S6K1, is frequently found in various cancers, including brain tumors.

As used herein, "receptor tyrosine kinase" (RTK) refers to a member of a group of tyrosine kinases that are also cell surface receptors. When RTKs bind to ligands, they may cross-link with other RTKs to form dimers, which activates the kinase activity of the intracellular kinase domain of the RTKs, resulting in intracellular signal cascades. As used herein, "TAM receptor" or "TAM family receptor tyrosine kinase" (and variations thereof) refers to a member of a family of RTKs that function as homeostatic regulators in adult tissues, including the nervous system. TAM receptors have an extracellular domain, a transmembrane domain, and an intracellular protein kinase domain. Overexpression of RTKs, including TAM receptors, is frequently observed in several types of cancers, including brain cancers such as glioblastomas.

As used herein, "LY2584702" is an ATP-competitive, small molecule inhibitor of S6K1. LY2584702 has the below chemical structure (compound 1):

Compound 1

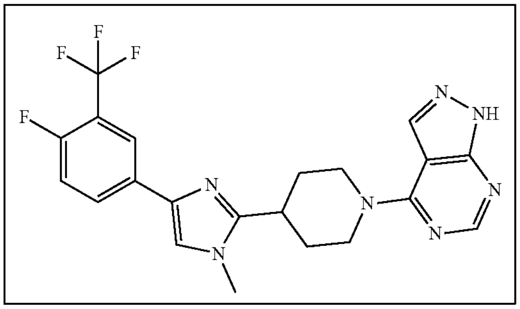

As used herein, "merestinib" is a small-molecule, ATP-competitive inhibitor of RTKs, including TAM receptors. Merestinib has the below chemical structure (compound 2):

Compound 2

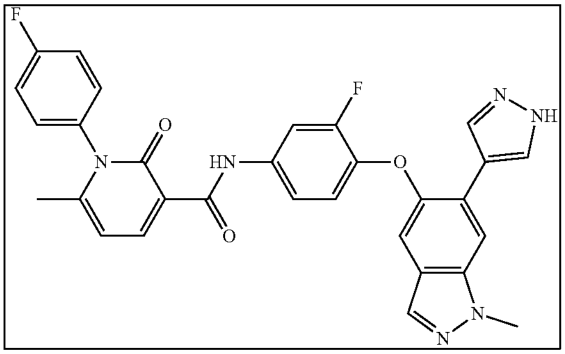

As used herein, "glioblastoma" refers to a tumor of the brain and/or spinal cord, originating from cell populations in the brain such as glial cells, astrocytes, oligodendrocytes, neural stem cells, or cells of an existing astrocytoma. Glioblastomas may be characterized by the presence of areas of necrotizing tissue, surrounded by anaplastic cells and hyperplastic blood vessels. Generally, glioblastomas are a highly aggressive form of cancer with a low survival rate. Symptoms associated with glioblastomas include, but are not limited to: headaches, seizures, double or blurred vision, sensory changes, cognitive issues, memory issues, concentration issues, changes in mood, changes in personality, alterations to speech, loss of balance and/or coordination, nausea, vomiting, loss of appetite, brain swelling, and alterations in pulse and/or breathing rates. As used herein "glioblastoma cell" (and variations thereof) refers to a cell in a glioblastoma tumor that exhibits the phenotype and/or genotype of the glioblastoma. Deletions of and/or mutations to the PTEN gene frequently occur in glioblastomas, and are correlated with therapeutic resistance of glioblastoma tumors. Glioblastomas can vary in severity and are graded on a scale from one to four, with grade 1 glioblastomas being the least aggressive and slowest growing, and grade 4 glioblastomas being the most aggressive and fastest growing. Primary glioblastomas (also known as de novo glioblastomas) are the most aggressive type of glioblastomas (generally, a grade 4), while also being the most common form of glioblastoma. Less common are secondary glioblastomas, which are slower growing and lower-grade than primary glioblastomas, and more commonly occur in younger people than primary glioblastomas.

In one embodiment, the present disclosure is directed to a method of inducing cell death in a phosphatase and tensin homolog (PTEN)-deficient glioblastoma cell, the method comprising administering to the cell a combination of therapeutic agents comprising: a therapeutically effective amount of merestinib and a therapeutically effective amount of LY2584702, wherein cell death of the glioblastoma cell is induced.

In another embodiment, the present disclosure is directed to a method of treating glioblastoma in a subject in need thereof, the method comprising administering to the subject a combination of therapeutic agents comprising: a therapeutically effective amount of merestinib and a therapeutically effective amount of LY2584702.

In another embodiment, the present disclosure is directed to a pharmaceutical composition comprising: a therapeutically effective amount of merestinib, a therapeutically effective amount of LY2584702, and one or more pharmaceutically acceptable excipients.

Methods of Treatment

In aspects, the present disclosure provides a method of inducing cell death in a phosphate and tensin homolog (PTEN)-deficient glioblastoma cell, the method comprising administering to the cell a combination of therapeutic agents comprising: a therapeutically effective amount of merestinib; and a therapeutically effective amount of LY2584702, wherein cell death of the glioblastoma cell is induced. In aspects, said method comprises administering the merestinib and the LY2584702 contemporaneously. In aspects, said method comprises administering the merestinib and the LY2584702 sequentially. For example, the merestinib may be administered first, and then the LY2584702 second; or the LY2584702 may be administered first, and then the merestinib second; or the merestinib and the LY2584702 may be administered in an alternating fashion.

In aspects, the present disclosure provides a method of inducing cell death in a phosphate and tensin homolog (PTEN)-deficient glioblastoma cell, the method comprising administering to the cell a combination of therapeutic agents comprising: a therapeutically effective amount of merestinib; and a therapeutically effective amount of LY2584702, wherein cell death of the glioblastoma cell is induced, and wherein the combination of therapeutic agents inactivates ribosomal protein S6 kinase 1 (S6K1) in the cell. In aspects, the present disclosure provides a method of inducing cell death in a phosphate and tensin homolog (PTEN)-deficient glioblastoma cell, the method comprising administering to the cell a combination of therapeutic agents comprising: a therapeutically effective amount of merestinib; and a therapeutically effective amount of LY2584702, wherein cell death of the glioblastoma cell is induced, and wherein the combination of therapeutic agents inactivates a receptor tyrosine kinase in the cell. In aspects, said receptor tyrosine kinase is a TAM family receptor tyrosine kinase.

In aspects, the present disclosure provides a method of inducing cell death in a phosphate and tensin homolog (PTEN)-deficient glioblastoma cell, the method comprising administering to the cell a combination of therapeutic agents comprising: a therapeutically effective amount of merestinib; and a therapeutically effective amount of LY2584702, wherein cell death of the glioblastoma cell is induced, and wherein the method is carried out in vitro. In aspects, the present disclosure provides a method of inducing cell death in a phosphate and tensin homolog (PTEN)-deficient glioblastoma cell, the method comprising administering to the cell a combination of therapeutic agents comprising: a therapeutically effective amount of merestinib; and a therapeutically effective amount of LY2584702, wherein cell death of the glioblastoma cell is induced, and wherein the method is carried out in vivo. In aspects wherein the method is carried out in vitro, the method is carried out in a glioblastoma cell or cell line. In aspects, said glioblastoma cell or cell line is a PTEN-deficient cell or cell line.

In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702. In aspects of said method, the glioblastoma comprises a PTEN-deficient glioblastoma.

In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702. In aspects, said method comprises administering the merestinib and the LY2584702 contemporaneously. In aspects, said method comprises administering the merestinib and the LY2584702 sequentially. For example, the merestinib may be administered first, and then the LY2584702 second; or the LY2584702 may be administered first, and then the merestinib second; or the merestinib and the LY2584702 may be administered in an alternating fashion.

In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents inactivates ribosomal protein S6 kinase 1 (S6K1) in the subject. In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents inactivates a receptor tyrosine kinase in the subject. In aspects, said receptor tyrosine kinase is a TAM family receptor tyrosine kinase.

In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents is administered to the subject orally. In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents is administered to the subject intravenously. In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents is administered to the subject parenterally. In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents is administered to the subject intrathecally. In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the combination of therapeutic agents is administered to the subject intramuscularly.

In aspects, the present disclosure provides a method of treating glioblastoma in a subject in need thereof, the method comprising administering to the subject a combination of therapeutic agents comprising: a therapeutically effective amount of merestinib and a therapeutically effective amount of LY2584702, and wherein the subject is a mammal. In aspects, the subject is a mouse. In aspects, the subject is a human.

In aspects, the present disclosure provides a method of treating glioblastoma in a subject in need thereof, the method comprising administering to the subject a combination of therapeutic agents comprising: a therapeutically effective amount of merestinib, a therapeutically effective amount of LY2584702, and one or more additional therapeutic agents. In aspects, the one or more additional therapeutic agents comprises one or more chemotherapeutic agents. In aspects, said one or more chemotherapeutic agents are selected from the group consisting of: temodar, vincristine, irinotecan, temozolomide, bevacizumab, BiCNU, hydroxyurea, carmustine, procarbazine, MVASI™ (bevacizumab-awwb) ZIRABEV™ (bevacizumab-bvzr), and combinations thereof.

The step of administering the active agents described herein may be initiated prior to, contemporaneous with, or after the onset of clinical symptoms in a subject with glioblastoma.

Pharmaceutical Compositions and Formulations

In aspects, a pharmaceutical composition or formulation is provided comprising a therapeutically effective amount of merestinib, a therapeutically effective amount of LY2584702, and one or more pharmaceutically acceptable carriers and/or excipients.

In aspects, a pharmaceutical composition or formulation comprises an adjuvant. In aspects, said pharmaceutical compositions are suitable for administration. Pharmaceutically acceptable carriers and/or excipients are determined in part by the particular composition being administered, as well as by the particular method used to administer the composition. Accordingly, there is a wide variety of suitable formulations of pharmaceutical compositions for administering the instantly disclosed compositions (see, e.g., *Remington's Pharmaceutical Sciences*, ($18^{TH}$ Ed, 1990), Mack Publishing Co., Easton, PA Publ)). In aspects, the pharmaceutical compositions are generally formulated as sterile, substantially isotonic, and in full compliance with all Good Manufacturing Practice (GMP) regulations of the U.S. Food and Drug Administration. Pharmaceutical compositions as disclosed herein are suitable for use in treatment of glioblastomas.

The terms "pharmaceutically acceptable," "physiologically tolerable," and grammatical variations thereof, as they refer to compositions, carriers, excipients, and reagents, are used interchangeably and represent that the materials are capable of administration to or upon a subject without the production of undesirable physiological effects to a degree that would prohibit administration of the composition. For example, "pharmaceutically acceptable excipient" means, for example, an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art would be able to determine the appropriate timing, sequence and dosages of administration for particular compounds and compositions of the present disclosure.

In aspects, preferred examples of such carriers or diluents include, but are not limited to, water, saline, Ringer's solutions, dextrose solution, and 5% human serum albumin. Liposomes and non-aqueous vehicles such as fixed oils can also be used. The use of such media and compounds for pharmaceutically active substances is well known in the art. Except insofar as any conventional media or compound is incompatible with the compounds and compositions of the present disclosure and as previously described above, use thereof in the compositions is contemplated. Supplementary active compounds can also be incorporated into the compositions.

In aspects, a pharmaceutical composition or formulation is provided comprising a therapeutically effective amount of merestinib, a therapeutically effective amount of LY2584702, and one or more pharmaceutically acceptable carriers and/or excipients. In aspects, said composition further comprises one or more additional therapeutic agents. In aspects, said one or more additional therapeutic agents comprises one or more chemotherapeutic agents. In aspects, said additional one or more chemotherapeutic agents is selected from the group consisting of: temodar, vincristine, irinotecan, temozolomide, bevacizumab, BiCNU, hydroxyurea, carmustine, procarbazine, MVASI™ (bevacizumab-awwb), ZIRABEV™ (bevacizumab-bvzr), and combinations thereof.

In aspects, pharmaceutical compounds and compositions of the present disclosure are formulated to be compatible with its intended route of administration. The pharmaceutical compounds and compositions of the present disclosure can be administered by parenteral, topical, intravenous, oral, subcutaneous, intraarterial, intradermal, transdermal, rectal, intracranial, intrathecal, intraperitoneal, intranasal; vaginally; intramuscular route or as inhalants. In aspects, pharmaceutical compounds and compositions of the present disclosure can be injected directly into a particular tissue, e.g., intracranial injection. In other aspects, intramuscular injection or intravenous infusion may be used for administration of pharmaceutical compounds and compositions of the present disclosure. In some methods, pharmaceutical compounds and compositions of the present disclosure are administered as a sustained release composition or device. In aspects, pharmaceutical compounds and compositions of the present disclosure are administered intradermally.

In aspects, pharmaceutical compounds and compositions of the present disclosure can optionally be administered in combination with other agents that are at least partly effective in treating various medical conditions as described herein.

In aspects, solutions or suspensions used for parenteral, intradermal, or subcutaneous application can include, but are not limited to, the following components: a sterile diluent such as water for injection, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. Examples of excipients can include starch, glucose, lactose, sucrose, gelatin, malt, rice, flour, chalk, silica gel, water, ethanol, DMSO, glycol, propylene, dried skim milk, and the like. The composition can also contain pH buffering reagents, and wetting or emulsifying agents.

In aspects, pharmaceutical compositions or formulations suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR™ EL (BASF, Parsippany, NJ) or phosphate buffered saline (PBS). In all cases, the composition is sterile and should be fluid to the extent that easy syringeability exists. It is stable under the conditions of manufacture and storage and is preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as mannitol, sorbitol, sodium chloride in the composition. Prolonged absorption of the injectable compositions can be brought about by including in the composition a compound that delays absorption, e.g., aluminum monostearate and gelatin.

For administration by inhalation, pharmaceutical compounds and compositions of the present disclosure can be delivered in the form of an aerosol spray from pressured container or dispenser that contains a suitable propellant, e.g., a gas such as carbon dioxide, or a nebulizer.

In aspects, systemic administration of the pharmaceutical compounds and compositions of the present disclosure can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the pharmaceutical compounds and compositions may be formulated into ointments, salves, gels, or creams and applied either topically or through transdermal patch technology as generally known in the art.

In aspects, the pharmaceutical compounds and compositions of the present disclosure can also be prepared in the form of suppositories (e.g., with conventional suppository bases such as cocoa butter and other glycerides) or retention enemas for rectal delivery.

In aspects, the pharmaceutical compounds and compositions of the present are prepared with carriers that protect the pharmaceutical compounds and compositions against rapid elimination from the body, such as a controlled-release formulation, including implants and microencapsulated delivery systems. Biodegradable, biocompatible polymers can be used, such as, for example, ethylene vinyl acetate, polyanhydrides, polyglycolic acid, collagen, polyorthoesters, and polylactic acid. Methods for preparation of such formulations will be apparent to those skilled in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art (U.S. Pat. No. 4,522,811, which is herein incorporated by reference in its entirety). In aspects, the pharmaceutical compounds and compositions of the present disclosure can be implanted within or linked to a biopolymer solid support that allows for the slow release of the pharmaceutical compounds and compositions to the desired site.

In aspects, it is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the instant disclosure are dictated by and directly dependent on the unique characteristics of the binding agent and the particular therapeutic effect to be achieved, and the limitations inherent in the art of compounding such pharmaceutical compounds and compositions for the treatment of a subject.

In aspects, compounds and compositions of the present disclosure can optionally be administered in combination with other agents that are at least partly effective in treating various medical conditions (e.g., glioblastomas) as described herein.

Active agents described herein can be co-administered (i.e., concurrently) or sequentially administered. When sequentially administered, the duration of time between administering a first active agent and administering a subsequent active agent may be from about 1 hour, 2 hours, 3 hours, 4 hours, 6 hours, 12 hours, 24 hours, one week, two weeks, three weeks, 4 weeks, one month, up to six months. In some embodiments, administration of one or more active agents as described herein is initiated prior to, contemporaneous with, or even after onset of motor symptoms in the subject. In a specific embodiment, administration is initiated during late stage ALS disease and is effective to slow disease progression and/or at least temporarily partially reverse motor symptoms in the subject, including paralysis. In another embodiment, administration is initiated after symptom onset, and more specifically after symptom onset and diagnosis.

In embodiments, the method further comprises treating the diagnosed subject with an effective amount of a therapeutic agent specific for the glioblastoma diagnosed.

EXAMPLES

The following examples are given by way of illustration are not intended to limit the scope of the disclosure.

Example 1. Combination of LY2584702 and Merestinib is Selectively Cytotoxic for PTEN-Deficient LN229 Glioblastoma Cells LN229 glioblastoma cells were transduced with either short hairpin RNA (shRNA) lentiviral particles coding for non-targeting shRNA (shNT) or shRNA that targets PTEN mRNA (shPTEN) for inhibition and degradation. These cells were then treated with either vehicle control, 10 μM LY2584702, 0.1-20 μM merestinib, or a combination of 10 μM LY2584702 and 0.1-20 μM merestinib. Cell viability was measured using CytoTox Glo after culturing with inhibitors in serum-free conditions for 72 hours.

As shown in FIG. 1, treatment with vehicle control, 10 μM LY2584702, or 0.1-20 μM merestinib was not cytotoxic for either shNT or shPTEN LN229 cells. On the other hand, a combination of 10 μM LY2584702 and 5-20 μM merestinib was cytotoxic for PTEN deficient shPTEN LN229 cells, while not significantly cytotoxic for shNT LN229 cells. These results demonstrate that the combination of LY2584702 and merestinib are selectively cytotoxic for PTEN deficient glioblastoma cells, while administration of either of these compounds alone has little impact on the viability of PTEN deficient glioblastoma cells.

Example 2. Combination of LY2584702 and Mrestinib is Selectively Cytotoxic for PTEN-Deficient U87MG Glioblastoma Cells U87MG glioblastoma cells were treated with doxycycline to induce PTEN expression (U-PTEN), while a separate set of U87 glioblastoma cells were treated with a similar amount of vector (U-vector). Thus, the U-vector cells were PTEN-deficient. These cells were then treated with either vehicle control, 10 μM LY2584702, 0.1-20 μM merestinib, or a combination of 10 μM LY2584702 and 0.1-20 μM merestinib. Cell viability was measured using CytoTox Glo after culturing with inhibitors in serum-free conditions for 72 hours.

Figure 2:
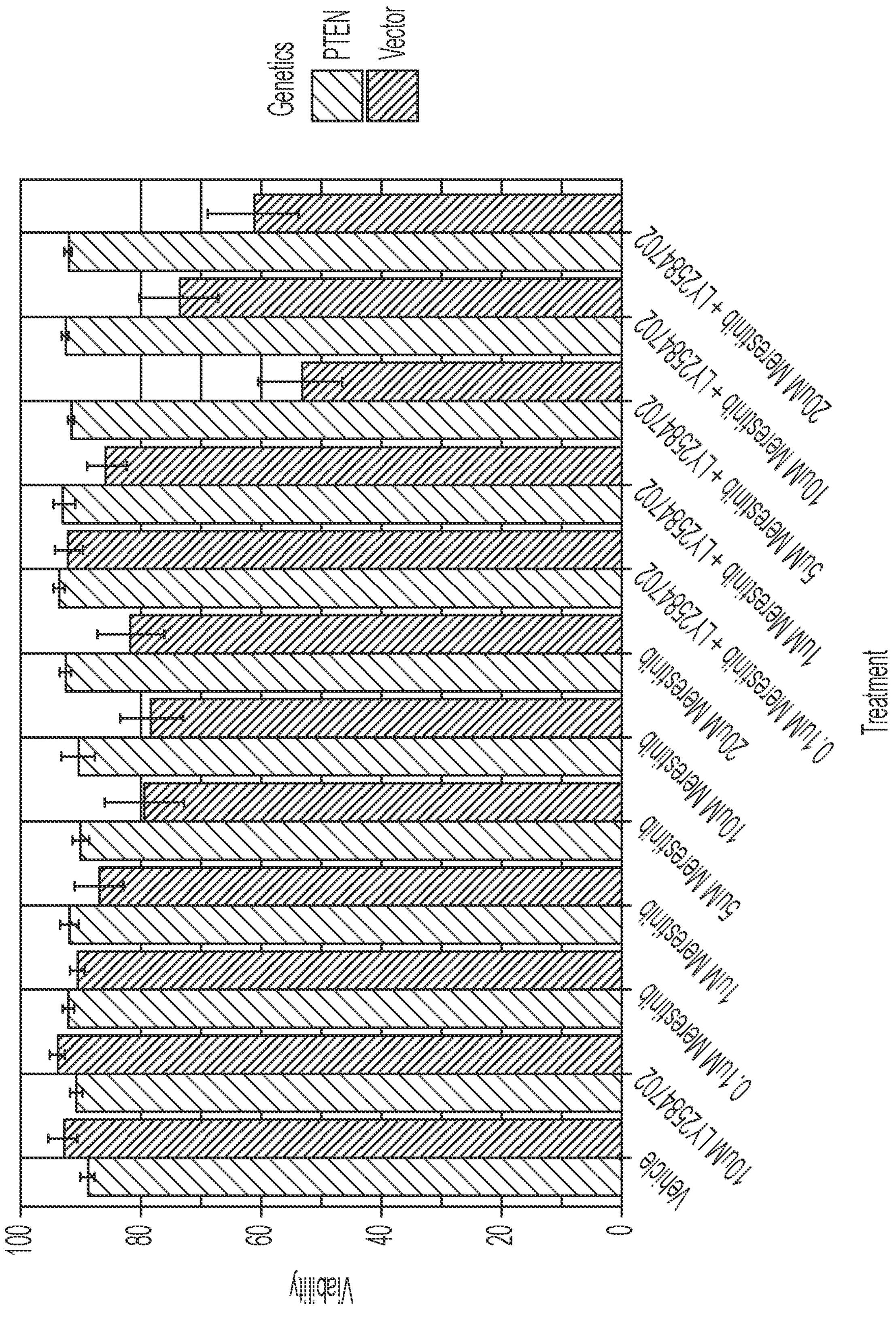
FIG. 2 depicts a dose curve analysis showing the efficacy of the combination of LY2584702 with merestinib in PTEN-deficient U87MG glioblastoma cells. Viability was measured using CytoTox Glo after culturing with inhibitors in serum-free conditions for 72 hours. Doxycycline addition induced PTEN and protected cells from the cytotoxic effect of combination drug treatment.

As shown in FIG. 2, treatment with vehicle control, 10 μM LY2584702, or 0.1-20 μM merestinib was not cytotoxic for either U-PTEN or U-vector U87MG glioblastoma cells. On the other hand, a combination of 10 μM LY2584702 and 5-20 μM merestinib was cytotoxic for PTEN-deficient U-vector U87MG glioblastoma cells, while not significantly cytotoxic for PTEN-expressing U-PTEN U87MG cells. These results demonstrate that the combination of LY2584702 and merestinib are selectively cytotoxic for PTEN deficient glioblastoma cells, while administration of either of these compounds alone has little impact on the viability of PTEN deficient glioblastoma cells.

Example 3. Other Combinations of TAM-Targeting Agents with S6K1 Inhibitors Fail to Exhibit Selectively Cytotoxicity for PTEN Deficient Glioblastoma Cells Glioblastoma cells were treated to produce two populations: PTEN-expressing and PTEN-deficient. These cells were then treated with either vehicle control, LY2584702, variable concentrations of cabozantinib, or a combination of LY2584702 and variable concentrations of cabozantinib. Cabozantinib is a small molecule inhibitor of RTKs, including TAM receptors. Cell viability was measured after culturing with the inhibitors.

Treatment with vehicle control, LY2584702, variable concentrations of cabozantinib, and or a combination of LY2584702 and variable concentrations of cabozantinib was not cytotoxic for either PTEN-expressing or PTEN-deficient glioblastoma cells.

Aspects

Aspects can be described with reference to the following numbered clauses, with preferred features laid out in dependent clauses.

1. A method of inducing cell death in a phosphate and tensin homolog (PTEN)-deficient glioblastoma cell, the method comprising administering to the cell a combination of therapeutic agents comprising:

a therapeutically effective amount of merestinib; and a therapeutically effective amount of LY2584702, wherein cell death of the glioblastoma cell is induced.

2. The method according to clause 1, wherein the merestinib and the LY2584702 are administered contemporaneously or sequentially.

3. The method according to any of the preceding clauses, wherein the combination of therapeutic agents inactivates ribosomal protein S6 kinase 1 (S6K1) in the cell.

4. The method according to any of the preceding clauses, wherein the combination of therapeutic agents inactivates TAM family receptor tyrosine kinase in the cell.

5. The method according to any of the preceding clauses, wherein the method is carried out in vitro or in vivo.

6. A method of treating glioblastoma in a subject in need thereof, the method comprising administering to the subject a combination of therapeutic agents comprising:

a therapeutically effective amount of merestinib; and a therapeutically effective amount of LY2584702.

7. The method according to clause 6, wherein the glioblastoma comprises PTEN-deficient glioblastoma.

8. The method according to any of clauses 6-7, wherein the merestinib and the LY2584702 are administered contemporaneously or sequentially.

9. The method according to any of clauses 6-8, wherein the combination of therapeutic agents inactivates ribosomal protein S6 kinase 1 (S6K1) in the subject.

10. The method according to any of clauses 6-9, wherein the combination of therapeutic agents inactivates TAM family receptor tyrosine kinase in the subject.

11. The method according to any of clauses 6-10, wherein the combination of therapeutic agents is administered orally, intravenously, parenterally, intrathecally, or intramuscularly.

12. The method according to any of clauses 6-11, wherein the subject is a mammal.

13. The method according to any of clauses 6-12, wherein the subject is a human.

14. The method according to any of clauses 6-13, further comprising administration of one or more additional therapeutic agents.

15. The method according to clause 14, wherein the one or more additional therapeutic agents comprises one or more chemotherapeutic agents.

16. The method according to clause 15, wherein the additional one or more chemotherapeutic agents is selected from the group consisting of temodar, vincristine, irinotecan, temozolomide, bevacizumab, BiCNU, hydroxyurea, carmustine, procarbazine, MVASI™ (bevacizumab-awwb), ZIRABEV™ (bevacizumab-bvzr), and combinations thereof.

17. A pharmaceutical composition comprising:

a therapeutically effective amount of merestinib;

a therapeutically effective amount of LY2584702; and one or more pharmaceutically acceptable excipients.

18. The pharmaceutical composition according to clause 17, further comprising an additional chemotherapeutic agent.

19. The pharmaceutical composition according to clause 18, wherein the additional chemotherapeutic agent is selected from the group consisting of temodar, vincristine, irinotecan, temozolomide, bevacizumab, BiCNU, hydroxyurea, carmustine, procarbazine, MVASI™ (bevacizumab-awwb), ZIRABEV™ (bevacizumab-bvzr), and combinations thereof.

20. The pharmaceutical composition according to any of clauses 17-19, formulated for oral, intravenous, parenteral, intrathecal, or intramuscular delivery.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

The foregoing description is illustrative of particular embodiments of the invention but is not meant to be a limitation upon the practice thereof. While particular embodiments have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A pharmaceutical composition comprising:

a therapeutically effective amount of merestinib;

a therapeutically effective amount of LY2584702; and one or more pharmaceutically acceptable excipients.

2. The pharmaceutical composition according to claim 1, further comprising an additional chemotherapeutic agent.

3. The pharmaceutical composition according to claim 2, wherein the additional chemotherapeutic agent is selected from the group consisting of temodar, vincristine, irinotecan, temozolomide, bevacizumab, BiCNU, hydroxyurea, carmustine, procarbazine, bevacizumab-awwb, bevacizumab-bvzr, and combinations thereof.

4. The pharmaceutical composition according to claim 1, formulated for oral, intravenous, parenteral, intrathecal, or intramuscular delivery.

5. A method of inducing cell death in a phosphate and tensin homolog (PTEN)-deficient glioblastoma cell, the method comprising administering to the cell a combination of therapeutic agents comprising:

a therapeutically effective amount of merestinib; and a therapeutically effective amount of LY2584702, wherein cell death of the PTEN-deficient glioblastoma cell is induced.

6. The method according to claim 5, wherein the merestinib and the LY2584702 are administered contemporaneously or sequentially.

7. The method according to claim 5, wherein the combination of therapeutic agents inactivates ribosomal protein S6 kinase 1 (S6K1) in the cell.

8. The method according to claim 5, wherein the combination of therapeutic agents inactivates TAM family receptor tyrosine kinase in the cell.

9. The method according to claim 5, wherein the method is carried out in vitro or in vivo.

10. A method of treating PTEN-deficient glioblastoma in a subject in need thereof, the method comprising administering to the subject a combination of therapeutic agents comprising:

a therapeutically effective amount of merestinib; and a therapeutically effective amount of LY2584702.

11. The method according to claim 10, wherein the merestinib and the LY2584702 are administered contemporaneously or sequentially.

12. The method according to claim 10, wherein the combination of therapeutic agents inactivates ribosomal protein S6 kinase 1 (S6K1) in the subject.

13. The method according to claim 10, wherein the combination of therapeutic agents inactivates TAM family receptor tyrosine kinase in the subject.

14. The method according to claim 10, wherein the combination of therapeutic agents is administered orally, intravenously, parenterally, intrathecally, or intramuscularly.

15. The method according to claim 10, wherein the subject is a mammal.

16. The method according to claim 15, wherein the subject is a mouse or a human.

17. The method according to claim 10, further comprising administration of one or more additional therapeutic agents.

18. The method according to claim 17, wherein the one or more additional therapeutic agents comprises one or more chemotherapeutic agents.

19. The method according to claim 2, wherein the one or more chemotherapeutic agents is selected from the group consisting of temodar, vincristine, irinotecan, temozolomide, bevacizumab, BiCNU, hydroxyurea, carmustine, procarbazine, bevacizumab-awwb, bevacizumab-bvzr, and combinations thereof.

* * * * *